(12) United States Patent
Eisinger et al.

(10) Patent No.: US 11,576,678 B2
(45) Date of Patent: Feb. 14, 2023

(54) CIRCULAR STAPLING DEVICE WITH ANVIL ROTATION LOCKING STRUCTURE

(71) Applicant: Covidien LP, Mansfield, MA (US)

(72) Inventors: Joseph Eisinger, Northford, CT (US); David Valentine, Hamden, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 17/498,973

(22) Filed: Oct. 12, 2021

(65) Prior Publication Data

US 2022/0039800 A1    Feb. 10, 2022

Related U.S. Application Data

(63) Continuation of application No. 16/550,935, filed on Aug. 26, 2019, now Pat. No. 11,141,163.

(60) Provisional application No. 62/741,319, filed on Oct. 4, 2018.

(51) Int. Cl.
    *A61B 17/064* (2006.01)
    *A61B 17/115* (2006.01)
    *A61B 17/072* (2006.01)

(52) U.S. Cl.
    CPC ........ *A61B 17/1155* (2013.01); *A61B 17/072* (2013.01); *A61B 2017/07228* (2013.01); *A61B 2017/07257* (2013.01); *A61B 2017/07271* (2013.01)

(58) Field of Classification Search
    CPC ...... A61B 17/1155; A61B 2017/00473; A61B 2017/07257
    USPC .......................................... 227/175.1, 175.2
    See application file for complete search history.

(56) References Cited

U.S. PATENT DOCUMENTS

| | | | |
|---|---|---|---|
| 3,388,847 | A | 6/1968 | Kasulin et al. |
| 3,552,626 | A | 1/1971 | Astafiev et al. |
| 3,638,652 | A | 2/1972 | Kelley |
| 3,771,526 | A | 11/1973 | Rudie |
| 4,198,982 | A | 4/1980 | Fortner et al. |
| 4,207,898 | A | 6/1980 | Becht |
| 4,289,133 | A | 9/1981 | Rothfuss |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

European Search Report dated Dec. 16, 2019, issued in EP Appln. No. 19201233, 9 pages.

*Primary Examiner* — Eyamindae C Jallow
(74) *Attorney, Agent, or Firm* — Carter, DeLuca & Farrell LLP (57) ABSTRACT

A circular stapling device includes an anvil assembly and an adaptor assembly including a shell assembly. The adaptor assembly includes an anvil retainer including an asymmetric tip. The anvil assembly has a center rod, an anvil head supported on the center rod, and an alignment member. The center rod has a proximal portion and a distal portion and defines a channel that extends from the proximal portion to the distal portion. The alignment member is positioned within the channel and is configured to engage the asymmetric trocar tip of the anvil retainer of the adaptor when the anvil assembly is attached to the anvil retainer to properly align the anvil assembly with the shell assembly.

20 Claims, 9 Drawing Sheets

(56) References Cited

U.S. PATENT DOCUMENTS

| | | |
|---|---|---|
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Mien et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Billner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |

(56) References Cited

U.S. PATENT DOCUMENTS

| | | |
|---|---|---|
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Dell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |

(56) References Cited

U.S. PATENT DOCUMENTS

| | | |
|---|---|---|
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 9,010,605 B2 * | 4/2015 | Olson ............... A61B 17/1155 227/176.1 |
| 10,111,668 B2 * | 10/2018 | Penna ............... A61B 17/1155 |
| 11,141,163 B2 | 10/2021 | Eisinger et al. |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0097025 A1 * | 5/2006 | Milliman ............... A61B 17/115 227/175.1 |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2007/0175963 A1 | 8/2007 | Bilotti et al. |
| 2009/0230170 A1 * | 9/2009 | Milliman ............... A61B 17/115 227/176.1 |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0170932 A1 * | 7/2010 | Wenchell ............ A61B 17/1155 227/176.1 |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 * | 5/2013 | Mozdzierz ......... A61B 17/1155 227/175.1 |
| 2013/0105546 A1 | 5/2013 | Milliman et al. |
| 2013/0105551 A1 | 5/2013 | Zingman |

(56) References Cited

U.S. PATENT DOCUMENTS

| | | |
|---|---|---|
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0131417 A1* | 5/2014 | Williams .............. A61B 17/068 227/175.3 |
| 2014/0151430 A1 | 6/2014 | Scheib et al. |
| 2014/0367444 A1* | 12/2014 | Williams ........... A61B 17/1155 227/175.1 |
| 2015/0129636 A1* | 5/2015 | Mulreed .............. A61B 17/115 227/177.1 |
| 2015/0297237 A1* | 10/2015 | Hafner ............... A61B 18/1445 606/49 |
| 2015/0305472 A1* | 10/2015 | Umar .................... A45D 26/00 606/133 |
| 2015/0305742 A1 | 10/2015 | Williams |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |
| 2017/0128068 A1 | 5/2017 | Zhang et al. |
| 2017/0360443 A1 | 12/2017 | Williams |
| 2018/0206846 A1* | 7/2018 | Guerrera ............. A61B 17/1155 |
| 2018/0242974 A1* | 8/2018 | Guerrera ............. A61B 17/1155 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 2656800 A1 | 10/2013 |
| EP | 3238638 A2 | 11/2017 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 9835614 A1 | 8/1998 |
| WO | 0154594 A1 | 8/2001 |
| WO | 2008107918 A1 | 9/2008 |

* cited by examiner

CIRCULAR STAPLING DEVICE WITH ANVIL ROTATION LOCKING STRUCTURE

CROSS-REFERENCE TO RELATED APPLICATIONS

This application is a continuation of U.S. patent application Ser. No. 16/550,935 filed Aug. 26, 2019, which claims the benefit of and priority to U.S. Provisional Patent Application Ser. No. 62/741,319 filed Oct. 4, 2018. The entire disclosure of each of these applications is incorporated by reference herein.

BACKGROUND

1. Technical Description

The present disclosure is directed to a circular stapling device, and more particularly, to a circular stapling device with structure to maintain rotational alignment between an anvil assembly and a shell assembly of the circular stapling device when the anvil assembly is attached to the circular stapling device.

2. Background of Related Art

Conventional circular stapling devices include a shell assembly having a circular staple cartridge and an anvil assembly having a circular anvil head. The circular staple cartridge includes a body defining a plurality of staple receiving pockets that receive staples. The circular anvil head defines staple deforming recesses that receive the staples during firing of the circular stapling device to form the staples. When the circular stapling device is fired, the staple receiving pockets of the staple cartridge must be properly aligned with the staple deforming recesses of the anvil head to properly form the staples within tissue.

Typically, the anvil assembly includes a center rod that supports the anvil head and the shell assembly includes a housing that defines an inner bore that receives the center rod when the anvil assembly and the shell assembly are approximated. In order to provide proper alignment between the anvil head and the staple cartridge, the center rod of the anvil assembly and the inner bore of the housing of the shell assembly include splines that mesh to cam and rotate the anvil head into alignment with staple cartridge.

In certain instances, the splines on the center rod of the anvil assembly crash head on into the splines on the housing of the shell assembly. When this occurs, the anvil head may not be properly aligned with the staple cartridge during firing of the circular stapling device. This may result in malformed staples which may result in ineffective sealing of tissue.

Accordingly, a continuing need exists in the stapling arts for a circular stapling device including improved structure to properly align the anvil with the staple cartridge to improve staple formation and operation of the stapling device.

SUMMARY

One aspect of the present disclosure is directed to a circular stapling device including an adaptor assembly and an anvil assembly. The adaptor assembly includes an elongate body, a shell assembly, and an anvil retainer. The anvil retainer includes a trocar having an asymmetric trocar tip. The shell assembly is supported on a distal portion of the elongate body and includes a staple cartridge and a housing. The staple cartridge includes a body supported on the housing defining an annular array of staple receiving pockets. The anvil assembly has a center rod, an anvil head, and an alignment member. The center rod has a proximal portion and a distal portion and a channel that extends from the proximal portion to the distal portion. The anvil head has an annular array of staple deforming pockets. The alignment member is positioned within the channel and is configured to engage the asymmetric trocar tip of the anvil retainer when the anvil assembly is attached to the anvil retainer to rotate the anvil assembly in relation to the trocar and move the annular array of staple receiving pockets into alignment with the annular array of staple deforming pockets.

Another aspect of the disclosure is directed to an anvil assembly including a center rod, and anvil head and an alignment member. The center rod has a proximal portion and a distal portion and defines a channel that extends from the proximal portion to the distal portion. The anvil head has an annular array of staple deforming pockets. The alignment member is positioned within the channel and is configured to engage an anvil retainer of a circular stapling device when the anvil assembly is attached to the anvil retainer to rotate the annular array of staple deforming pockets into alignment with the circular stapling device.

In embodiments, the stapling device includes a handle assembly that supports a proximal portion of the elongate body.

In some embodiments, the alignment member includes a distal face and a plurality of protrusions that are spaced about the distal face.

In certain embodiments, the protrusions define recesses there between, wherein the recesses are configured to receive the trocar tip of the anvil retainer when the anvil assembly is attached to the anvil retainer.

In embodiments, each of the protrusions has a triangular configuration and includes a side wall that defines in part one of the recesses.

In some embodiments, the side wall is angled and is positioned to engage the trocar tip as the trocar tip is advanced into the channel such that continued advancement of the trocar tip into the channel after the trocar tip engages the angled side wall causes the alignment member and the anvil assembly to rotate in relation to the trocar to move the annular array of staple receiving pockets into alignment with the annular array of staple deforming pockets.

In certain embodiments, the alignment member includes a distal face having a plurality of concavities that are spaced about the distal face.

In embodiments, each of the concavities has a spherical configuration.

In some embodiments, the trocar tip has a spherical configuration.

In certain embodiments, the proximal portion of the center rod includes a plurality of resilient fingers, wherein each of the resilient fingers has an inner surface that defines a portion of the channel.

In embodiments, each of the resilient fingers includes a rib and the trocar defines a recess, wherein the rib of each of the resilient fingers is received within the recess of the trocar to releasably secure the anvil assembly to the trocar.

In some embodiments, the housing includes an inner housing portion defining a bore that is configured to receive the center rod and the center rod supports at least one first spline. In certain embodiments, the inner housing portion includes a plurality of second splines extending into the bore that define channels there between, wherein the at least one first spline is positioned to be received in the channels of the inner housing portion.

In embodiments, the alignment member is positioned to rotate the anvil assembly in relation to the trocar to move the at least one first spline into alignment with one of the channels defines between the plurality of second splines.

BRIEF DESCRIPTION OF THE DRAWINGS

Various embodiments of the presently disclosed circular stapling device are described herein below with reference to the drawings, wherein.

DETAILED DESCRIPTION OF EMBODIMENTS

The presently disclosed circular stapling device will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. Further, the term "clinician" is used generally to refer to medical personnel including doctors, nurses, and support personnel.

Figure 1:
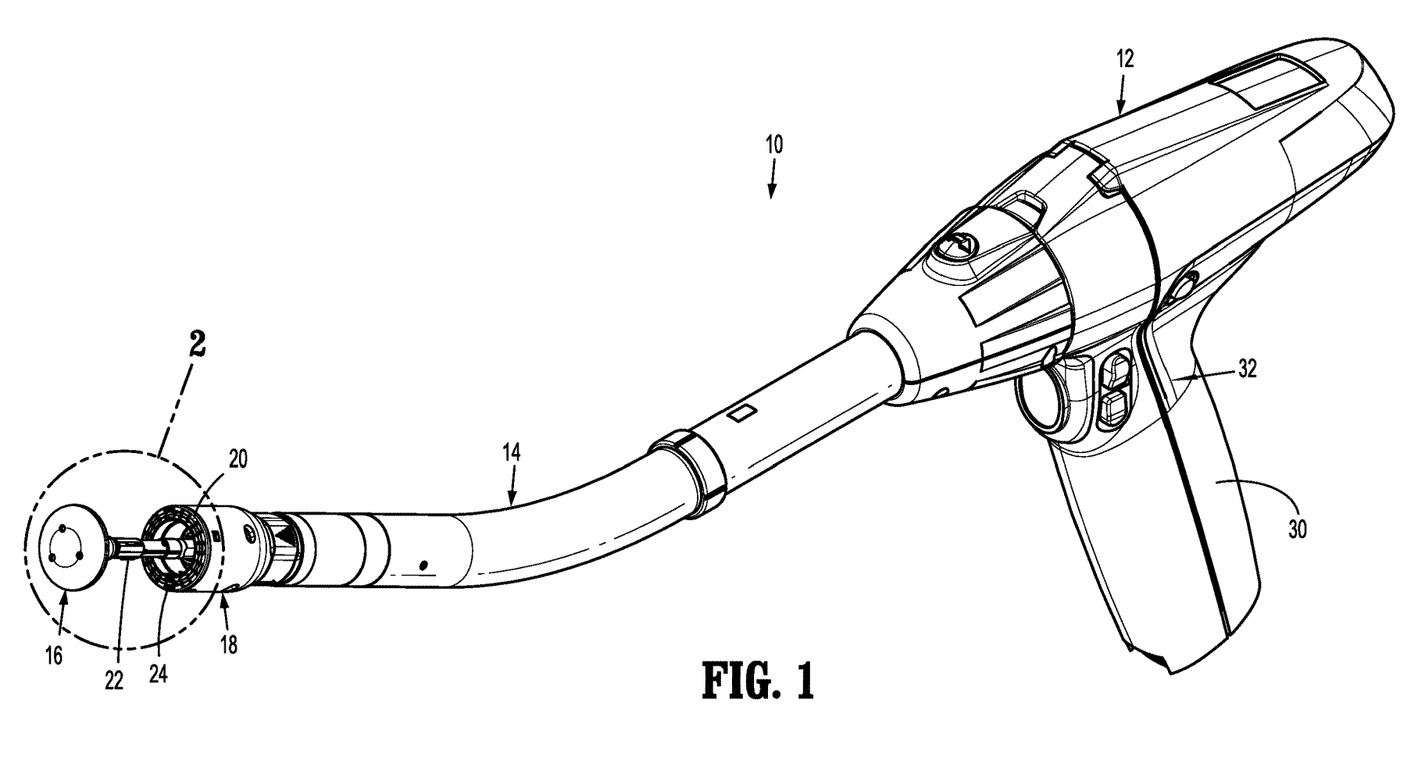
FIG. 1 is a side perspective view of an exemplary embodiment of the presently disclosed circular stapling device with the anvil in an unapproximated position.
Figure 2:
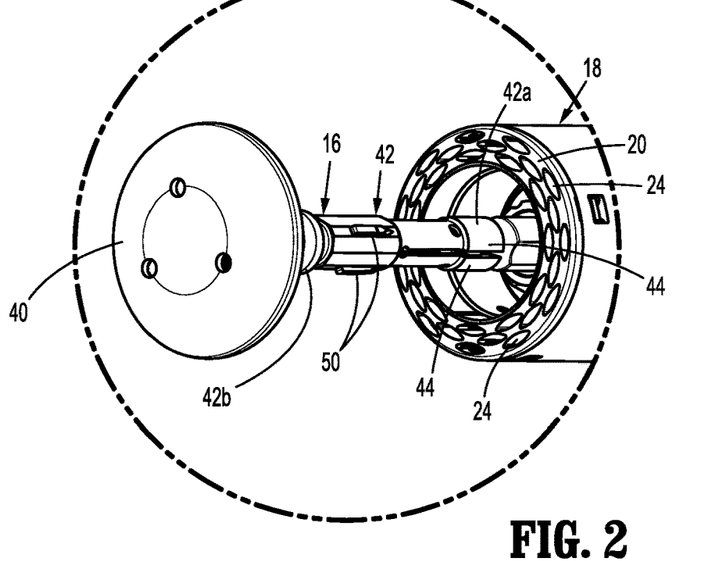
FIG. 2 is an enlarged view of the area of detail shown in FIG. 1.
Figure 3:
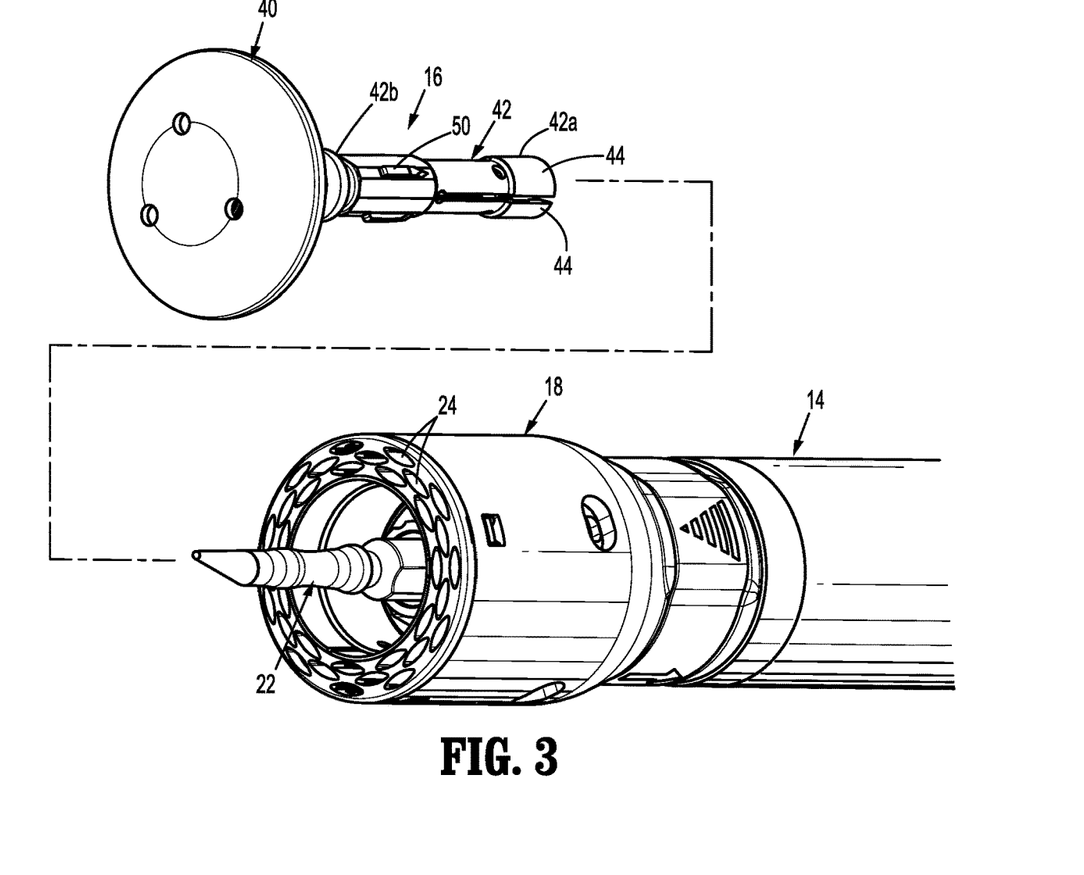
FIG. 3 is a side perspective view of a distal portion of the adaptor and the anvil assembly of the circular stapling device shown in FIG. 1 with parts separated.
Figure 4:
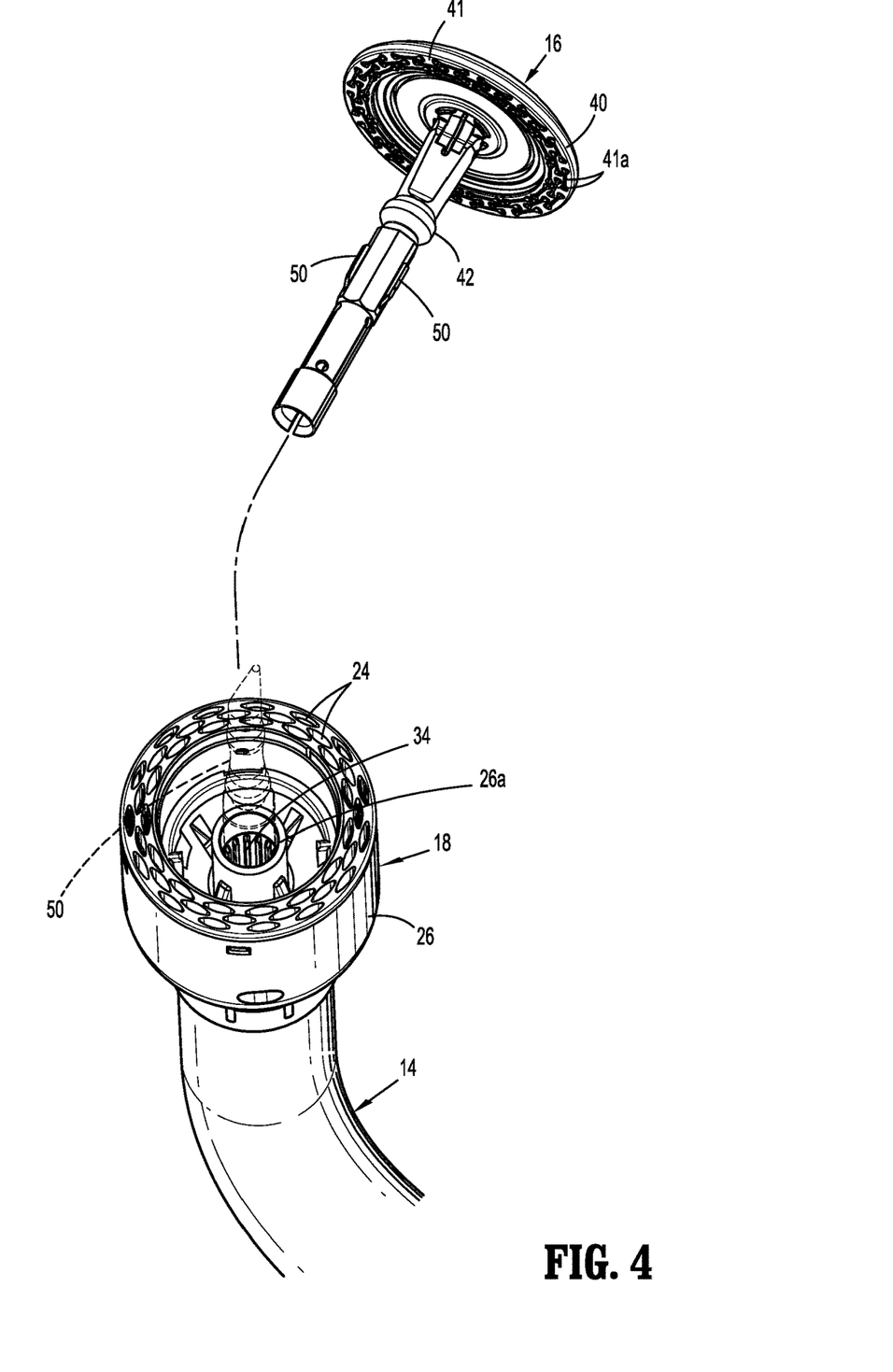
FIG. 4 is a side perspective view of the distal portion of the adaptor and the anvil assembly of the circular stapling device shown in FIG. 3 with parts separated with the trocar of the adaptor shown in phantom.

FIG. 1 illustrates a circular stapling device shown generally as stapling device 10. The stapling device 10 includes a handle assembly 12, an elongate body or adaptor assembly 14, and an anvil assembly 16. The adaptor assembly 14 includes an elongate body 17, a shell assembly 18, and an anvil retainer 22 that is configured to releasably support the anvil assembly 16. The shell assembly 18 has a proximal portion supported on a distal portion of the elongate body 17 and a distal portion that supports a staple cartridge 20. The staple cartridge 20 defines a plurality of annular rows of staple receiving pockets 24. Each of the staple receiving pockets 24 receives a staple (not shown) such that the staple cartridge 20 supports annular rows of staples.

The handle assembly 12 is illustrated as a powered assembly and includes a stationary grip 30 and actuation buttons 32 for controlling operation of stapling device functions including approximation of the anvil and shell assemblies 16, 18, respectively, and firing of staples (not shown) from the staple cartridge 20 of the shell assembly 18. The adaptor assembly 14 is coupled to the handle assembly 12 to translate power from the handle assembly 12 to the anvil and shell assemblies 16, 18. Although the present disclosure illustrates powered handle and adaptor assemblies 12, 14, respectively, it is envisioned that the advantages of the present disclosure as described in detail below are also applicable to circular stapling devices having manually operated handle and adaptor assemblies. U.S. Pat. No. 7,303,106 ("the '106 Patent") discloses an example of a surgical stapling device including a manually actuated handle assembly and is incorporated herein by reference in its entirety. U.S. Pat. No. 9,023,014 ("the '014 Patent") and U.S. Pat. No. 9,055,943 ("the '943 Patent") disclose examples of surgical stapling devices including exemplary powered handle assemblies. Each of these patents is incorporated herein by reference in its entirety.

Figure 5:
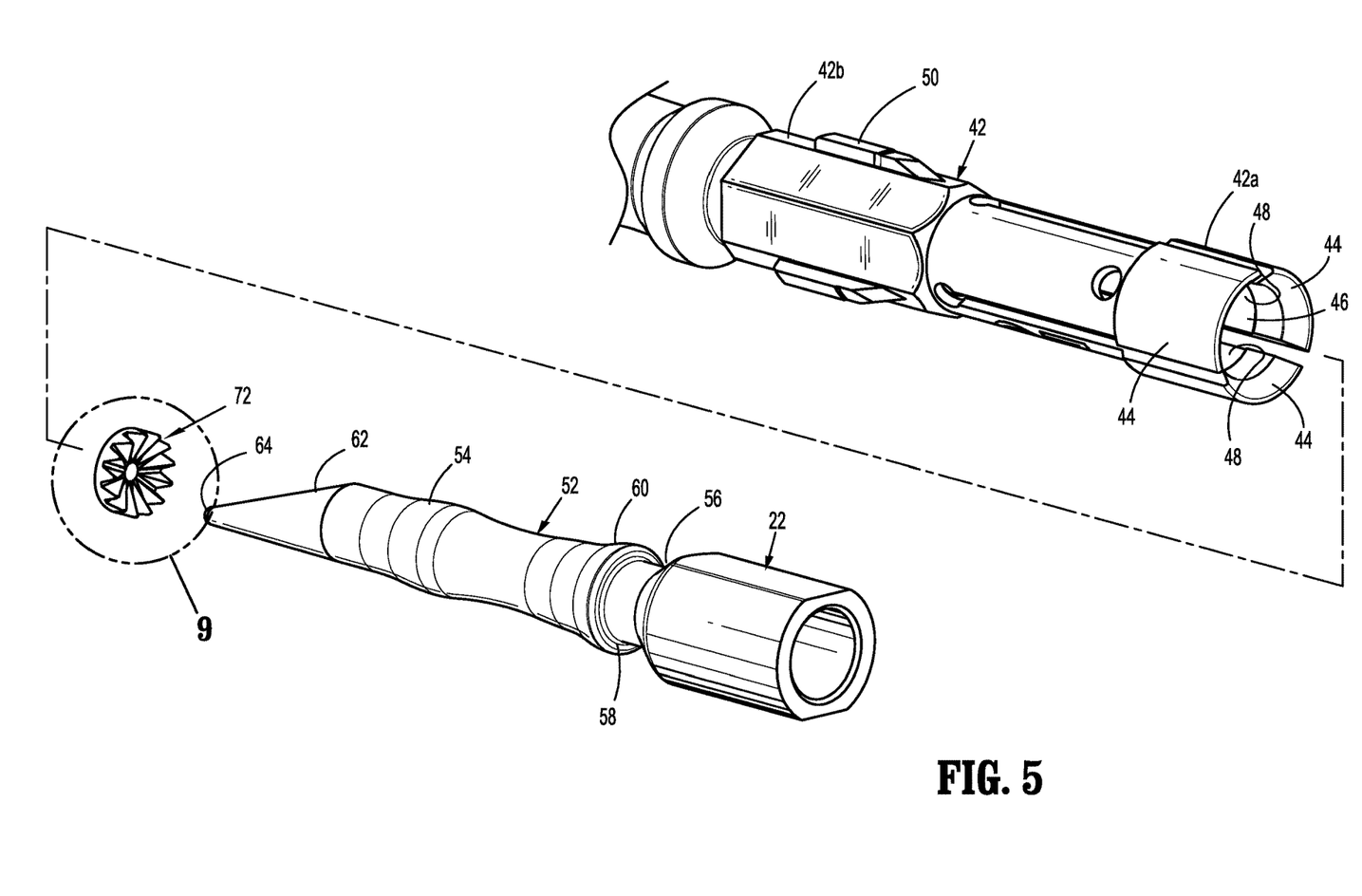
FIG. 5 is a side perspective view of a proximal portion of a center rod of the anvil assembly, an alignment member, and the trocar of the adaptor assembly of the circular stapling device shown in FIG. 4 with parts separated.
Figures 6, 7, 8:
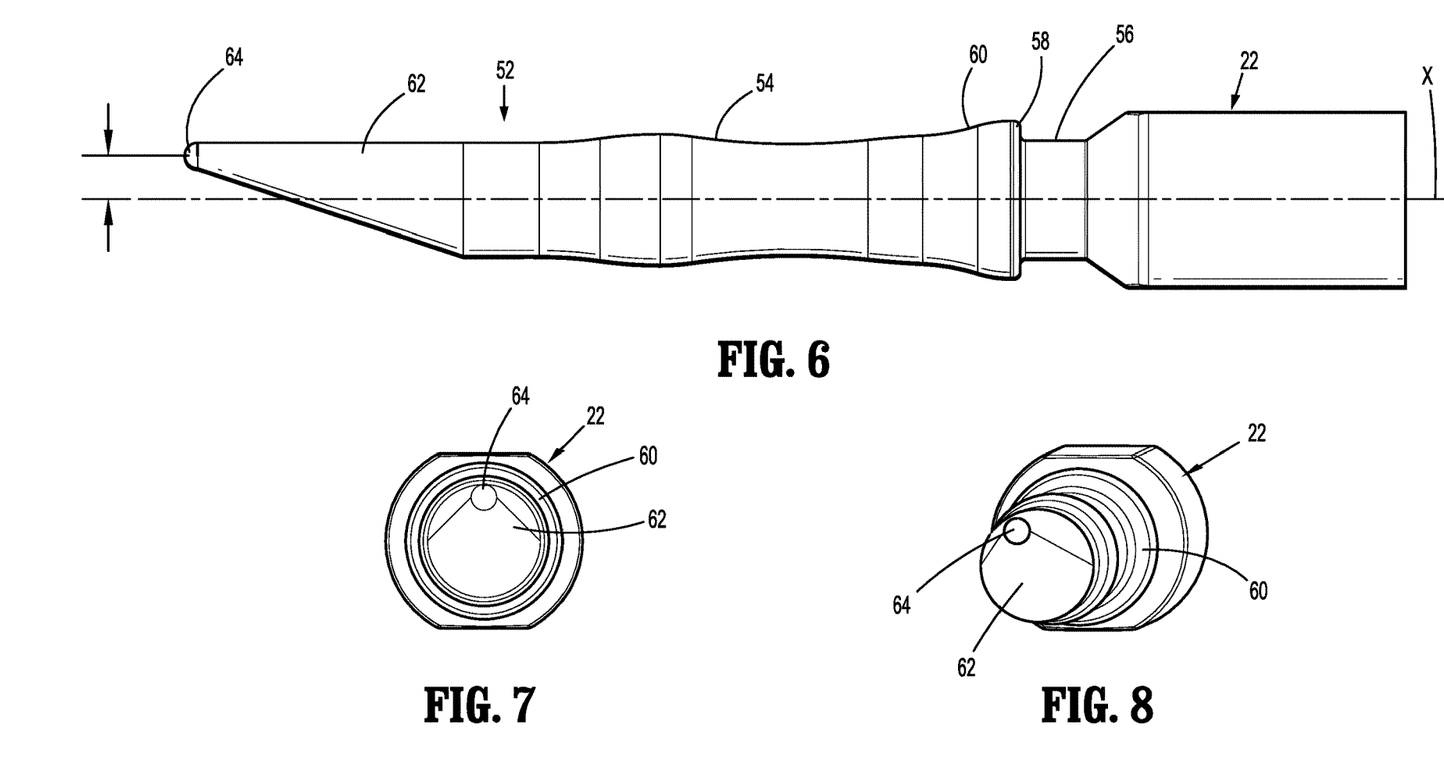
FIG. 6 is a side view of the trocar of the adaptor shown in FIG. 5.
FIG. 7 is a front view of the trocar shown in FIG. 6.
FIG. 8 is a side perspective view from the distal end of the trocar shown in FIG. 8.

Referring to FIGS. 2-5, the anvil assembly 16 includes an anvil head 40 and an anvil center rod 42 having a proximal portion 42a and a distal portion 42b. The distal portion 42b of the anvil center rod 42 is coupled to the anvil head 40. The proximal portion 42a of the center rod 42 includes a plurality of resilient fingers 44. The distal portion 42b and the resilient fingers 44 of the anvil center rod 42 define a central channel 46 (FIG. 5) that is dimensioned to receive the anvil retainer 22 of the adaptor assembly 14 as described in further detail below. Each of the resilient fingers 44 includes an inner surface that defines a rib 48 (FIG. 5). The ribs 48 of the resilient fingers 44 together define an annular engagement surface that is positioned to engage the anvil retainer 22 to releasably secure the anvil assembly 16 to the anvil retainer 22. The anvil center rod 42 also supports one or more splines 50 that are positioned between the anvil head 40 and the resilient fingers 44. The splines 50 function to maintain alignment between the anvil assembly 16 and the shell assembly 18 after the anvil and shell assemblies 16, 18 are approximated to facilitate proper formation of staples when the stapling device 10 (FIG. 1) is approximated and fired as described in further detail below.

The anvil head 40 supports a circular anvil 41 (FIG. 4) that defines a plurality of annular rows of staple deforming recesses 41a. Each of the staple deforming recesses 41a is configured to receive the legs of a respective staple (not shown) to properly form the staples into a desired configuration, e.g., B-shape. In order to accomplish this function, the staple deforming recesses 41a must be properly aligned with the staple receiving pockets 24 of the staple cartridge 20 to receive the legs of the staples.

Referring to FIG. 5, the shell assembly 18 includes a housing 26 having an inner housing portion 26a defining a bore 28 that receives the anvil retainer 22 as the anvil retainer 22 is translated between approximated and unapproximated positions. The inner housing portion 26a includes splines 34 that define channels between adjacent splines 34. The channels defined between the splines 34 receive the splines 50 of the center rod 42 of the anvil assembly 16 to maintain alignment between the anvil assembly 16 and the shell assembly 18 during approximation and firing of the stapling device 10. For a more detailed description of the approximation assembly of the stapling device 10, see, e.g., the '106, '014, and '943 Patents which are incorporated herein by reference.

Although not described in detail herein, the anvil head 40 can be mounted to the anvil center rod 42 in a pivotal manner to facilitate pivotal movement of the anvil head 40 in relation to the anvil center rod 42 between operative and inoperative (tilted) positions. Alternately, the anvil head 40 can be fixedly secured to the anvil center rod 42 in the operative position.

Referring also to FIGS. 5-8, in embodiments, the anvil retainer 22 includes a trocar 52 having a body 54 defining a longitudinal axis "X". The body 54 is connected to an approximation assembly (not shown) supported within the adaptor assembly 14 (FIG. 1). For a more detailed description of the approximation assembly of the adaptor assembly 14, see, e.g., the '014 and '943 Patents which are incorporated herein by reference. The body 54 defines an annular recess 56 that is defined in part by a shoulder 58, and a tapered body portion 60 (FIG. 6) that is positioned immediately distal to the annular recess 56. The tapered body portion 60 of the body 54 of the trocar 52 has a diameter that increases in a proximal direction along a length of the trocar 52. The shoulder 58 is positioned on the trocar 52 to engage the ribs 48 on the resilient fingers 44 of the anvil center rod 42 to releasably secure the trocar 52 to the anvil center rod 42. More specifically, when the trocar 52 is inserted into the channel 46 of the anvil center rod 42 (FIG. 11), the resilient fingers 44 of the anvil center rod 42 engage the tapered body portion 60 of the trocar 52 and are flexed outwardly as the trocar 52 is advanced into the channel 46. When the ribs 48 of the resilient fingers 44 pass proximally over the shoulder 58 of the trocar 52, the resilient fingers 44 snap inwardly to position the ribs 48 in engagement with the shoulder 58 of the trocar 52 to releasably secure the anvil center rod 42 about the trocar 52. The annular recess 56 extends entirely about the center rod 42. As such, receipt of the ribs 48 within the recess 56 does not prohibit rotation of the anvil assembly 16 in relation to the trocar 52.

The body 54 of the trocar 52 includes a distal tapered trocar portion 62 including a trocar tip 64. In embodiments, the tapered trocar portion 62 is asymmetric such that the trocar tip 64 is positioned at a location offset from the longitudinal axis "X". In embodiments, the trocar tip 64 is rounded or blunt. Alternately, the trocar tip 64 can have a sharper configuration to more effectively pierce tissue.

Figure 9:
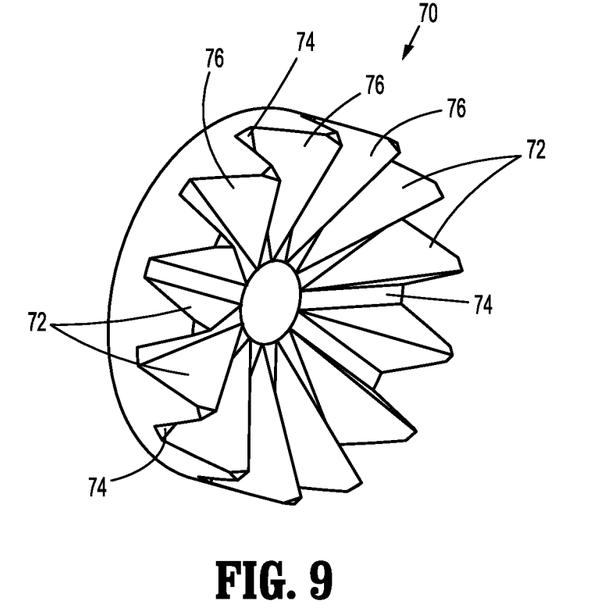
FIG. 9 is an enlarged view of the indicated area of detail shown in FIG. 5.
Figure 10:
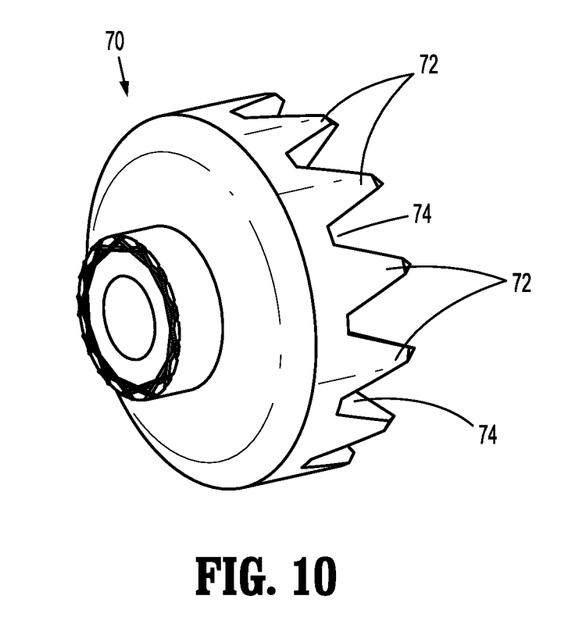
FIG. 10 is a side perspective view from the distal end of the alignment member shown in FIG. 9.

Referring to FIGS. 5, 9, and 10, an alignment member 70 is fixedly supported in the channel 46 (FIG. 5) in the distal portion 42b of the anvil center rod 42. The alignment member 70 includes a plurality of protrusions 72 that are spaced apart about a distal face of the alignment member 70. The protrusions 72 define valleys or recesses 74 between each of the adjacent protrusions 72. In embodiments, the protrusions 72 have a triangular configuration and include angled walls 76 that are positioned to engage the trocar tip 64 of the trocar 52 when the anvil assembly 16 is received on the trocar 52. Alternately, it is envisioned that the protrusions 72 may have a variety of configurations to achieve the objectives summarized below.

Figure 11:
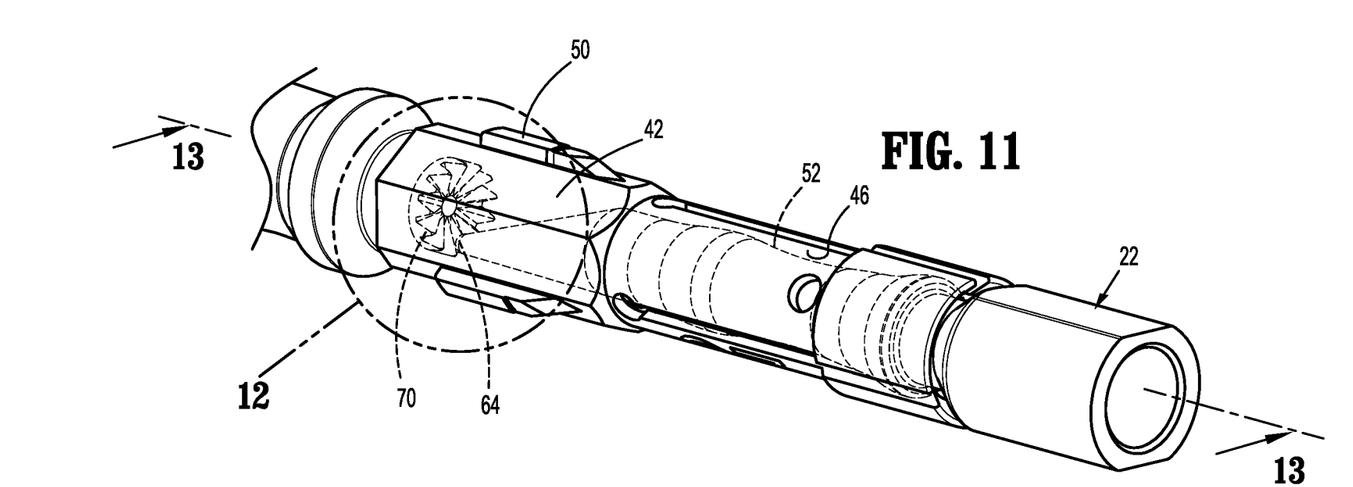
FIG. 11 is a side perspective view of the proximal portion of the center rod, the alignment member, and the trocar of the circular stapling device shown in FIG. 5 assembled with the trocar shown in phantom.
Figure 12:
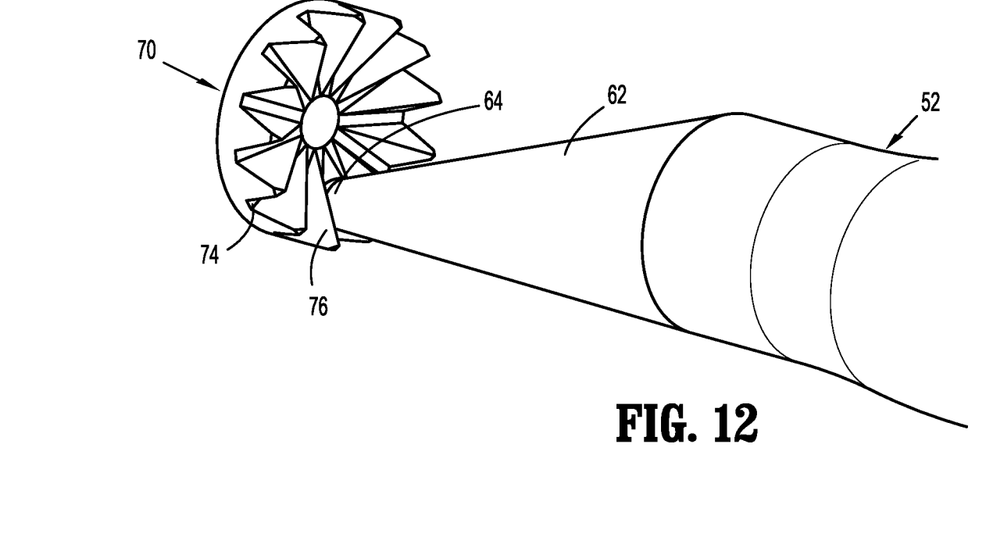
FIG. 12 is an enlarged view of the indicated area of detail shown in FIG. 11.
Figure 13:
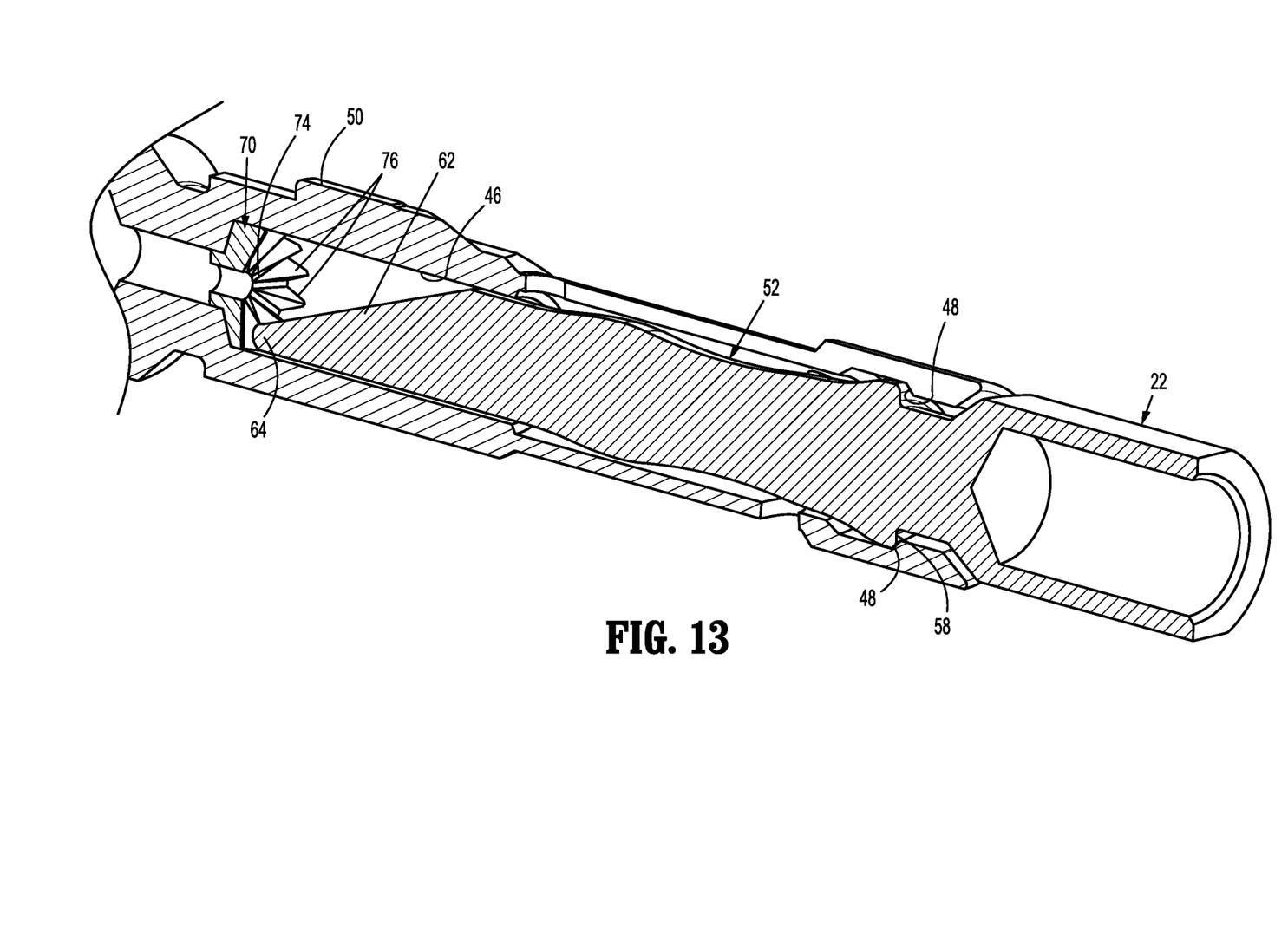
FIG. 13 is a cross-sectional view taken along section lines 13-13 of FIG. 12.

Referring also to FIGS. 11-13, the alignment member 70 is positioned within the channel 46 in the distal portion 42b of the center rod 42. In embodiments, the alignment member 70 includes an insert that is secured within the channel 46 by welding or the like. Alternately, the alignment member 70 can be integrally formed with the center rod 42 or secured within the channel 46 of the center rod 42 using any of a variety of known fastening techniques.

When the trocar 52 is advanced into the channel 46 of the anvil center rod 42 to couple the anvil assembly 16 to the anvil retainer 22, the trocar tip 64 is dimensioned to engage the protrusions 72 of the alignment member 70 as the anvil assembly 16 is coupled to the trocar 52. When the trocar tip 64 engages one of the angled walls 76 of a respective one of the protrusions 72, continued advancement of the trocar 22 into the channel 46 of the center rod 42 cams the alignment member 70 into rotation about the longitudinal axis "X" of the trocar 52. Since the alignment member 70 is fixed within the channel 46 of the center rod 42 of the anvil assembly 16, rotation of the alignment member 70 causes the anvil assembly 16 to rotate in relation to the trocar 52 to position the anvil assembly 16 in proper alignment with the shell assembly 18. In this position, the splines 50 on the center rod 42 and the splines 34 on the inner housing portion 26 of the housing 26 of the shell assembly 18 are positioned to mesh without crashing. When the trocar tip 52 bottoms out in one of the recesses 74 of the alignment member 70, the trocar tip 64 is dimensioned to engage adjacent protrusions 72 in a manner to prevent further rotation of the anvil assembly 16 about the trocar 52 (FIG. 12).

Figure 14:
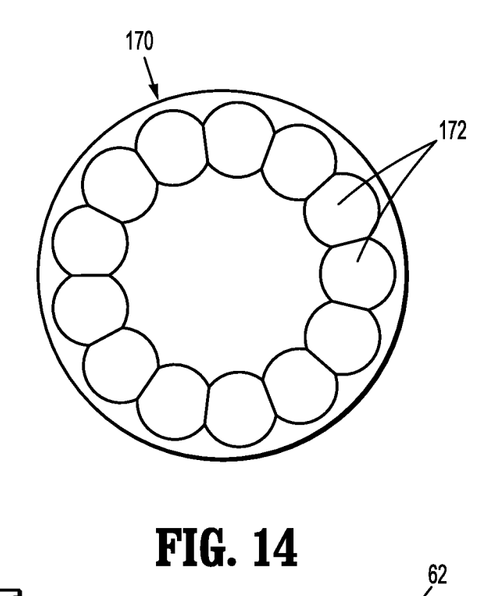
FIG. 14 is a view from the proximal end of another embodiment of the alignment member of the presently disclosed circular stapling device shown in FIG. 1.
Figure 15:
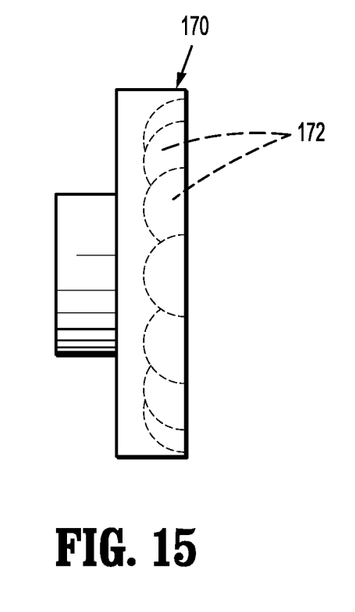
FIG. 15 is a side view of the alignment member shown in FIG. 1.
Figure 16:
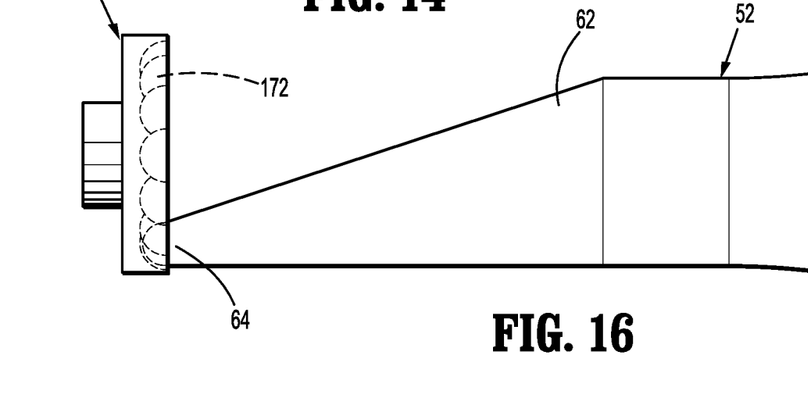
FIG. 16 is a side view of the alignment member shown in FIG. 15 engaged with the trocar of the adaptor shown in FIG. 6.

FIGS. 14-16 illustrate another exemplary embodiment of an alignment member of the presently disclosed circular stapling device 10 (FIG. 1) shown generally as alignment member 170. The alignment member 170 includes a distal face that defines a circular array of recesses or concavities 172. Each of the concavities 172 have a configuration that corresponds to the shape of the trocar tip 64. In use, when the trocar tip 64 is received within one of the concavities 172, engagement between the trocar tip 64 and side walls defining the concavity 172 will cam the alignment member 170 into rotation about the trocar 52 to move the anvil assembly 16 (FIG. 2) into alignment with the staple cartridge 20 of the shell assembly 18. When the trocar tip 64 bottoms out within a respective protrusion 172 of the alignment member 170, engagement between the trocar tip 64 and the alignment member 170 prevents further rotation of the alignment member 170 in relation to the trocar 52 and, thus prevents further rotation of the anvil assembly 16 in relation to the staple cartridge 20 of the shell assembly 18.

As discussed above in regard to the alignment member 70 (FIG. 5), the alignment member 170 can be formed integrally with the center rod 42 of the anvil assembly 16, or, in the alternative, separately as an insert that is positioned within the channel 46 (FIG. 5) in the distal portion 42b of the center rod 42 and subsequently secured to the center rod 42. In embodiments, the concavities 172 in the alignment member 170 are substantially spherical in shape. Alternately, it is envisioned that the concavities 172 may assume a variety of different configurations. In embodiments, the trocar tip 64 and the concavities 172 each have a substantially spherical configuration.

Although the presently disclosed circular stapling device is shown to include both splines 34, 50 on the shell and anvil assemblies 18, 16 and an alignment member 70, 170, it is envisioned that the circular stapling device need only include the alignment member 70, 170 and the asymmetric trocar 52 to effect and maintain alignment between the anvil assembly 16 and the staple cartridge 20 of the shell assembly 18.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An anvil retainer comprising:
   a body defining a central longitudinal axis and having a proximal end and a distal trocar portion, the body defining an annular recess that is positioned between the distal trocar portion and the proximal end, the annular recess being defined in part by a shoulder, the distal trocar portion having an asymmetric configuration and including a trocar tip that is positioned outwardly of the central longitudinal axis of the body.

2. The anvil retainer of claim 1, wherein the body includes a proximal portion that includes the proximal end of the body, the proximal portion configured to be coupled to a surgical stapling device.

3. The anvil retainer of claim 1, wherein the body includes a tapered portion that is positioned distally of and adjacent to the annular recess, the tapered portion having a diameter that increases in a proximal direction.

4. The anvil retainer of claim 1, wherein the trocar tip is rounded or blunt.

5. A circular stapling device comprising:
   an adaptor assembly including an elongate body and an anvil retainer, the elongate body having a proximal portion and a distal portion, the anvil retainer extending from the distal portion of the elongate body and including a body defining a central longitudinal axis, the body having a proximal end and a distal trocar portion, the body defining an annular recess that is positioned between the distal trocar portion and the proximal end, the annular recess being defined in part by a shoulder, the distal trocar portion having an asymmetric configuration and including a trocar tip that is positioned outwardly of the central longitudinal axis of the body.

6. The circular stapling device of claim 5, further including a shell assembly supported on the distal portion of the elongate body, the shell assembly including a staple cartridge and a housing, the staple cartridge including a body supported on the housing, the body defining an annular array of staple receiving pockets.

7. The circular stapling device of claim 6, further including an anvil assembly, the anvil assembly including a center rod, an anvil head, and an alignment member, the center rod having a proximal portion and a distal portion and defining a channel that extends from the proximal portion to the distal portion, the anvil head having an annular array of staple forming pockets, the alignment member being positioned within the channel and configured to engage the trocar tip of the anvil retainer when the anvil assembly is attached to the anvil retainer, engagement of the alignment member with the trocar tip rotating the anvil assembly in relation to the anvil retainer to move the annular array of staple receiving pockets into alignment with the annular array of staple deforming pockets.

8. The circular stapling device of claim 7, further including a handle assembly supported on the proximal portion of the elongate body.

9. The circular stapling device of claim 8, wherein the alignment member defines recesses positioned between the protrusions, the recesses configured to receive the trocar tip of the anvil retainer when the anvil assembly is attached to the anvil retainer.

10. The circular stapling device of claim 9, wherein each of the protrusions has a triangular configuration and includes a side wall that defines in part one of the recesses.

11. The circular stapling device of claim 10, wherein the side wall is angled and is positioned to engage the trocar tip as the trocar tip is advanced into the channel such that continued advancement of the trocar tip into the channel after the trocar tip engages the angled side wall causes the alignment member and the anvil assembly to rotate in relation to the trocar to move the annular array of staple receiving pockets into alignment with the annular array of staple deforming pockets.

12. The circular stapling device of claim 7, wherein the alignment member includes a distal face and a plurality of protrusions that are spaced about the distal face.

13. The circular stapling device of claim 7, wherein the alignment member includes a distal face having a plurality of concavities that are spaced about the distal face.

14. The circular stapling device of claim 13, wherein each of the concavities has a spherical configuration.

15. The circular stapling device of claim 14, wherein the trocar tip has a spherical configuration.

16. The circular stapling device of claim 7, wherein the proximal portion of the center rod includes a plurality of resilient fingers, each of the resilient fingers having an inner surface that defines a portion of the channel.

17. The circular stapling device of claim 16, wherein each of the resilient fingers includes a rib that is received within the annular recess of the of the body of the anvil retainer to releasably secure the anvil assembly to the anvil retainer.

18. The circular stapling device of claim 17, wherein the housing includes an inner housing portion defining a bore, the bore configured to receive the center rod.

19. The circular stapling device of claim 18, wherein the center rod supports at least one first spline and the inner housing portion includes a plurality of second splines that extend into the bore, the plurality of second splines defining channels there between, the at least one first spline received within the channels of the inner housing portion.

20. The circular stapling device of claim 19, wherein the alignment member is positioned to rotate the anvil assembly in relation to the trocar to move the at least one first spline into alignment with one of the channels defined between the plurality of second splines.

\* \* \* \* \*